United States Patent [19]

Harris et al.

[11] Patent Number: 5,349,094

[45] Date of Patent: Sep. 20, 1994

[54] PROCESS FOR THE PRODUCTION OF OLIGOGLYCEROL MIXTURES OF INCREASED DIGLYCEROL CONTENT

[75] Inventors: Eugene G. Harris, West Chester, Ohio; Udo Hees, Mayen, Fed. Rep. of Germany; Reinhard Bunte, Dormagen, Fed. Rep. of Germany; Johannes W. Hachgenei, Duesseldorf, Fed. Rep. of Germany; Peter Kuhm, Hilden, Fed. Rep. of Germany

[73] Assignee: Henkel Kommanditgesellschaft auf Aktien, Duesseldorf, Fed. Rep. of Germany

[21] Appl. No.: 898,061

[22] Filed: Jun. 12, 1992

[51] Int. Cl.$^5$ ............................................. C07C 41/09
[52] U.S. Cl. .................................. 568/619; 568/679; 568/680; 568/698
[58] Field of Search ............... 568/619, 679, 680, 698

[56] References Cited

U.S. PATENT DOCUMENTS 3,033,778  5/1962  Frilette ........................... 568/698
4,960,953 10/1990  Jakobson et al. .

FOREIGN PATENT DOCUMENTS 0333984  9/1989  European Pat. Off. .

OTHER PUBLICATIONS

J. Am. Oil. Chem. Soc. 66, 153 (1989).

*Primary Examiner*—Howard T. Mars
*Attorney, Agent, or Firm*—Ernest G. Szoke; Wayne C. Jaeschke; Frank S. Chow

[57] ABSTRACT

Oligoglycerol mixtures having a high diglycerol content are prepared by a process in which glycerol is condensed in the presence of zeolites corresponding to formula (I)

$$M_{2/z}O * Al_2O_3 * x\, SiO_2 * y\, H_2O \qquad (I)$$

in which M is an alkali metal or alkaline earth metal having a valency of z, x is a number of 1.8 to 12 and y is a number of 0 to 8. The water of condensation which is formed during the reaction, is continuously removed from the reaction mixture and the reaction is terminated when the quantity of water theoretically necessary for the formation of diglycerol has been separated.

10 Claims, No Drawings

PROCESS FOR THE PRODUCTION OF OLIGOGLYCEROL MIXTURES OF INCREASED DIGLYCEROL CONTENT

FIELD OF THE INVENTION

This invention relates to a process for the production of oligoglycerol mixtures having an increased diglycerol content, in which glycerol is condensed in the presence of zeolites at elevated temperature.

DESCRIPTION OF THE PRIOR ART

Diglycerol has acquired considerable significance as a starting material for the production of fatty acid esters. Esters such as these are used as emulsifiers in the food industry and in cosmetics and for various industrial applications, for example as lubricants or stabilizers for PVC [J. Am. Oil. Chem. Soc. 66, 153 (1989)].

Diglycerol is generally produced from glycerol by reaction with glycidol [Fette, Seifen, Anstrichmitt., 88, 101 (1986)] or epichlorohydrin [EP 0 333 984 A1]. However, this reaction is by no means selective. Also, the starting glycidol and epichlorohydrin are difficult to handle necessitating stringent work safety measures.

Alternatively, glycerol may be condensed in the presence of alkali bases. However, this process is not entirely satisfactory because the reaction yields mixtures which, in addition to diglycerol, also contain undesirable products such as higher homologs and significant quantities of unreacted glycerol. Moreover, the diglycerol has to be separated from these mixtures by distillation which is very time- and energy-consuming. For this reason, it would be highly advantageous to produce oligoglycerol mixtures which have a high diglycerol content. In view of the large quantities of diglycerol produced on an industrial or commercial scale, an increase in the diglycerol content of only around 1% would represent an economically significant advance.

Also, in the catalytic production of oligoglycerol it is always a problem to remove the catalyst from the final product. This adds further to the cost of manufacture of this important chemical.

Accordingly, the present invention is directed to provide an improved process for the production of oligoglycerol mixtures of increased diglycerol content.

DESCRIPTION OF THE INVENTION

The present invention relates to a process for the production of oligoglycerol mixtures of increased diglycerol content, characterized in that glycerol is condensed in the presence of zeolites corresponding to formula (I)

$$M_{2/z}O * Al_2O_3 * x\ SiO_2 * y\ H_2O \qquad (I)$$

in which M is an alkali metal or alkaline earth metal having a valency of z, x is a number of 1.8 to 12 and y is a number of 0 to 8.

The water of condensation which is formed during the reaction is continuously removed from the reaction mixture and the reaction is terminated when the quantity of water theoretically necessary for the formation of diglycerol has been separated.

It has surprisingly been found that zeolites not only catalyze the self-condensation of glycerol, they also promote the formation of oligoglycerol mixtures which have an increased diglycerol content and a reduced ash content in relation to the prior art. In contrast to the catalysts used in the prior art, these catalysts are insoluble in the reaction mixture and may readily be removed on completion of the reaction, yielding low-solids oligoglycerol mixtures.

The reaction can also be carried out using a fixed reaction bed.

In the context of the process according to the invention, zeolites are understood to be optionally water-containing alkali metal or alkaline earth metal aluminosilicates corresponding to general formula (I). These compounds may be of natural or synthetic origin. Typical examples are the naturally occurring minerals such as clinoptilolite, erionite or chabasite and the like. However, preferred zeolites are synthetic zeolites, for example

| zeolite X | $Na_{86}[(AlO_2)_{86}(SiO_2)_{106}] * 264\ H_2O$ |
|---|---|
| zeolite Y | $Na_{56}[(AlO_2)_{56}(SiO_2)_{136}] * 325\ H_2O$ |
| zeolite L | $K_9[AlO_2)_9(SiO_2)_{27}] * 22\ H_2O$ |
| mordenite | $Na_{8.7}[(AlO_2)_{8.7}(SiO_2)_{39.3}] * 24\ H_2O$ |
| and, more particularly, | |
| zeolite A | $Na_{12}[(AlO_2)_{12}(SiO_2)_{12}] * 27\ H_2O$ |

The zeolites may be used in the condensation reaction in quantities of 1 to 10% by weight and preferably in quantities of 2 to 5% by weight, based on the glycerol. The temperature at which the condensation of the glycerol is carried out may be in the range from 200° to 250° C.

To carry out the condensation reaction, the glycerol and zeolites are initially introduced into the reaction gas atmosphere. To displace the equilibrium, the water of condensation which is formed during the reaction is removed, for example via a water separator. The reaction is terminated when the quantity of water theoretically necessary for the formation of diglycerol has been separated off. In general, the reaction time is 1 to 39 h and preferably 3 to 25 h. The catalyst is then removed from the reaction mixture, for example by pressure filtration.

The diglycerol may be separated from the oligoglycerol mixture formed, for example by distillation in a high vacuum. For many applications, however, the oligoglycerol mixtures according to the invention may be used without further separation.

Industrial Applications

The oligoglycerol mixtures of increased diglycerol content obtainable by the process according to the invention are suitable for the production of chemical products, more particularly fatty acid esters, and as emulsifiers in foods and cosmetic products in which they may be present in quantities of 0.1 to 25% by weight and preferably in quantities of 1 to 10% by weight, based on the preparation as a whole.

The following Examples are intended to illustrate the invention without limiting it in any way.

EXAMPLES

EXAMPLE 1

552.0 g (6 mol) glycerol and 13.3 g zeolite NaA (Wessalith CD, a product of Degussa AG, Frankfurt/FRG)—corresponding to 2.4% by weight, based on the glycerol—were introduced into a 1-liter three-necked flask equipped with a reflux condenser and water separator and heated for 22 h to 240° C. under a nitrogen blanket. The reaction product was then cooled and filtered off through a pressure nutsche (operating pressure: 3 bar). The oligoglycerol mixture accumulating as filtrate had the following composition:
15.4% by weight glycerol
32.3% by weight diglycerol
20.5% by weight triglycerol
31.8% by weight higher oligoglycerol mixtures
Ash content (incineration for 2 h at 800° C.): 0.5% by weight.

EXAMPLE 2

Example 1 was repeated using 552 g glycerol and 13.3 g zeolite NaZ granules (Zeolite 13X, a product of Union Carbide, USA). The oligoglycerol mixture accumulating after removal of the catalyst insoluble in the reaction mixture had the following composition:
9.5% by weight glycerol
27.6% by weight diglycerol
20.0% by weight triglycerol
42.9% by weight higher oligoglycerol mixtures
Ash content (incineration for 2 h at 800° C.): 0.6% by weight.

EXAMPLE 3

Example 1 was repeated using 552g glycerol and 13.3 g zeolite NaX powder (Zeolite 13X, a product of Union Carbide, USA). The oligoglycerol mixture accumulating after removal of the catalyst insoluble in the reaction mixture had the following compositions:
9.6% by weight glycerol
30.9% by weight diglycerol
22.0% by weight triglycerol
37.5% by weight higher oligoglycerol mixtures
Ash content (incineration for 2 h at 800° C.): 1.2% by weight.

COMPARISON EXAMPLE C1

Example 1 was repeated using 552 g glycerol and 13.3 g sodium silicate (NaSKS6, a product of Hoeschst AG, Frankfurt/FRG). The catalyst dissolved in glycerol and could not be separated off after the reaction. The resulting oligoglycerol mixture had the following composition:
8.5% by weight glycerol
29.7% by weight diglycerol
23.0% by weight triglycerol
38.8% by weight higher oligoglycerol mixtures
Ash content (incineration for 2 h at 800° C.): 2.6% by weight.

What is claimed is:

1. A process for the production of oligoglycerol mixtures of increased diglycerol content which comprises condensing glycerol in the presence of zeolites having the formula (I)

$$M_{2/z}O * Al_2O_3 * x\, SiO_2 * y\, H_2O \qquad (I)$$

in which M is an alkali metal or alkaline earth metal having a valency of z, x is a number of 1.8 to 12 and y is a number of 0 to 8, removing continuously the water of condensation, which is formed during the reaction, from the reaction mixture and terminating the reaction when the quantity of water theoretically necessary for the formation of diglycerol has been separated.

2. A process as claimed in claim 1, wherein the zeolites are selected from the group consisting of zeolite X, zeolite Y, zeolite L, Zeolite A and mordenite are used.

3. A process as claimed in claim 1 wherein the zeolites are used in quantities of 1 to 10% by weight, based on the glycerol.

4. The process as claimed in claim 2 wherein the zeolites are used in quantities of 1 to 10% by weight, based on the glycerol.

5. A process as claimed in claim 1 wherein the condensation is carried out at temperature of 200° to 260° C.

6. The process as claimed in claim 2 wherein the condensation is carried out at temperature of 200° to 260° C.

7. A process as claimed in claim 1 wherein the zeolites are separated from the oligoglycerol mixture after the reaction.

8. A process according to claim 1 wherein M is sodium.

9. A process according to claim 1 wherein the zeolite is selected from $$Na_{86}[(AlO_2)_{86}(SiO_2)_{106}] * 264\ H_2O$$

$$Na_{56}[(AlO_2)_{56}(SIO_2)_{136}] * 325\ H_2O$$

or $Na_{8.7}[(AlO_2)_{8.7}(SiO_2)_{39.3}] * 24\ H_2O$.

10. The process as claimed in claim 2 wherein the zeolite is select from $$Na_{86}[(AlO_2)_{86}(SiO_2)_{106}] * 264\ H_2O$$

$$Na_{56}[(AlO_2)_{56}(SIO_2)_{136}] * 325\ H_2O$$

or $Na_{8.7}[(AlO_2)_{8.7}(SiO_2)_{39.3}] * 24\ H_2O$.

* * * * *